(12) United States Patent
Glenn et al.

(10) Patent No.: US 11,738,003 B2
(45) Date of Patent: Aug. 29, 2023

(54) METHOD FOR ADMINISTRATION

(71) Applicant: Hoffmann-La Roche Inc., Nutley, NJ (US)

(72) Inventors: Kellie Glenn, Roseland, NJ (US); Brian Higgins, Fresh Meadows, NY (US); Gwen Nichols, New York, NY (US); Kathryn Packman, Bloomfield, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 93 days.

(21) Appl. No.: 16/951,153

(22) Filed: Nov. 18, 2020

(65) Prior Publication Data

US 2021/0069149 A1  Mar. 11, 2021

Related U.S. Application Data

(63) Continuation of application No. 16/510,256, filed on Jul. 12, 2019, now abandoned, which is a continuation of application No. 14/596,747, filed on Jan. 14, 2015, now abandoned, which is a continuation of application No. 13/759,647, filed on Feb. 5, 2013, now abandoned.

(60) Provisional application No. 61/612,429, filed on Mar. 19, 2012.

(51) Int. Cl.
*A61K 31/401* (2006.01)
*A61K 31/40* (2006.01)
*A61K 9/14* (2006.01)

(52) U.S. Cl.
CPC ............ *A61K 31/401* (2013.01); *A61K 9/146* (2013.01); *A61K 31/40* (2013.01)

(58) Field of Classification Search
CPC .......... A61K 31/40; A61K 9/10; A61K 9/146; A61K 9/284
See application file for complete search history.

(56) References Cited

U.S. PATENT DOCUMENTS 9,216,170 B2   12/2015   Higgins et al.

FOREIGN PATENT DOCUMENTS

| WO | 2008076415 A1 | 6/2008 |
| WO | 2011098398 A1 | 8/2011 |

OTHER PUBLICATIONS

The English translation of the Chinese Office Action, dated Jul. 13, 2021, in the related Chinese Appl. No. 201910030832.0.
(Continued)

*Primary Examiner* — San Ming R Hui

(57) ABSTRACT

There is provided a new dosage regimen for Compound A which maximizes anti-tumor activity while maintaining acceptable toxicity levels.

11 Claims, 2 Drawing Sheets

(56) References Cited

OTHER PUBLICATIONS

The English translation of the Chinese Office Action, dated Mar. 11, 2022, in the related Chinese patent application No. 201910030832.0.

Ohnstad et al., "MDM2 antagonist Nutlin-3a potentiates antitumour activity of cytotoxic drugs in sarcoma cell lines," BMC Cancer, May 30, 2011;11:211:1-11.

Canner et al., "MI-63: a novel small-molecule inhibitor targets MDM2 and induces apoptosis in embryonal and alveolar rhabdomyosarcoma cells with wild-type p53," Br J Cancer, Sep. 1, 2009;101(5):774-81.

The English translation of the Korean Office Action, dated Nov. 2, 2020, in the related Korean Appl. No. 2019-7008801.

Terry Priestman, "Cancer Chemotherapy in Clinical Practice," Springer, 2008, pp. 24 to 27.

The English translation of the Brazilian Examination Report, dated Sep. 20, 2021, in the related Brazilian Appl. No 12 2020 002189-6.

METHOD FOR ADMINISTRATION

CROSS-REFERENCE TO RELATED APPLICATIONS

This application is a Continuation application Ser. No. 16/510,256, filed Jul. 12, 2019, which is a Continuation of application Ser. No. 14/596,747, filed Jan. 14, 2015, which is a Continuation of application Ser. No. 13/759,647, filed Feb. 5, 2013, which claims the benefit of U.S. Provisional Application No. 61/612,429, filed Mar. 19, 2012. Each of these applications is incorporated by reference herein in its entirety.

FIELD OF THE INVENTION

The present invention is related to improved methods of administration of 4-{[(2R,3S,4R,5S)-4-(4-Chloro-2-fluoro-phenyl)-3-(3-chloro-2-fluoro-phenyl)-4-cyano-5-(2,2-dim-ethyl-propyl)-pyrrolidine-2-carbonyl]-amino}-3-methoxy-benzoic acid (referred to herein as Compound A) in the treatment of cancer. In particular, the invention relates to improved methods of administration of Compound A that provide desirable antineoplastic effects with a tolerable level of toxicity. The methods of the invention are characterized by administering less frequent doses comprising relatively high concentrations of Compound A. This protocol is expected to be safer and at least as effective as, possibly more effective than, administering more frequent doses at lower concentrations or larger doses at intermittent periods.

BACKGROUND OF THE INVENTION

Compound A is an orally administered pyrrolidine that inhibits the binding of MDM2 to p53 and is thus useful in the treatment of cancer. It has the following chemical structure:

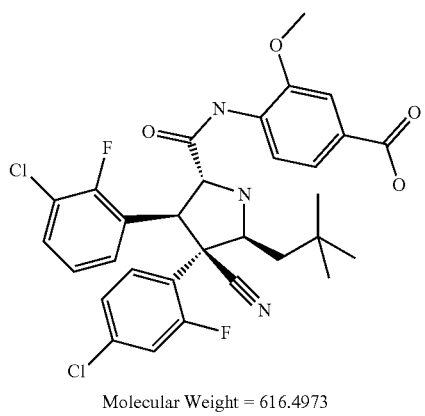

Molecular Weight = 616.4973
Molecular Formula = C31H29Cl2F2N3O4

Compound A recently entered into phase I clinical trials for the treatment of solid tumors. See ClinicalTrials.gov, identifier NCT01462175. This compound is disclosed in US Pub 2010/0152190 A1. To the extent necessary, this patent publication is herein incorporated by reference.

Applicants have discovered that Compound A is especially effective, and best tolerated, in cancer therapy when administered in the specific doses and pursuant to the specific protocols herein described.

SUMMARY OF THE INVENTION

The present invention relates to a method of treating a patient suffering with cancer, in particular colon, breast, prostate, lung or kidney cancer or osteosarcoma, comprising administering to the patient Compound A in an amount of from about 800 to about 3000 mg/day, or from about 1000 to about 2500 mg/day, or from about 1250 to about 1800 mg/day, for an administration period of up to about 7 days, preferably up to about 5 days, on days 1-7, or preferably days 1-5, of a 28 day treatment cycle, followed by a rest period of from about 21 to about 23 days, preferably up to about 23 days.

DETAILED DESCRIPTION OF THE INVENTION

Figure 1:
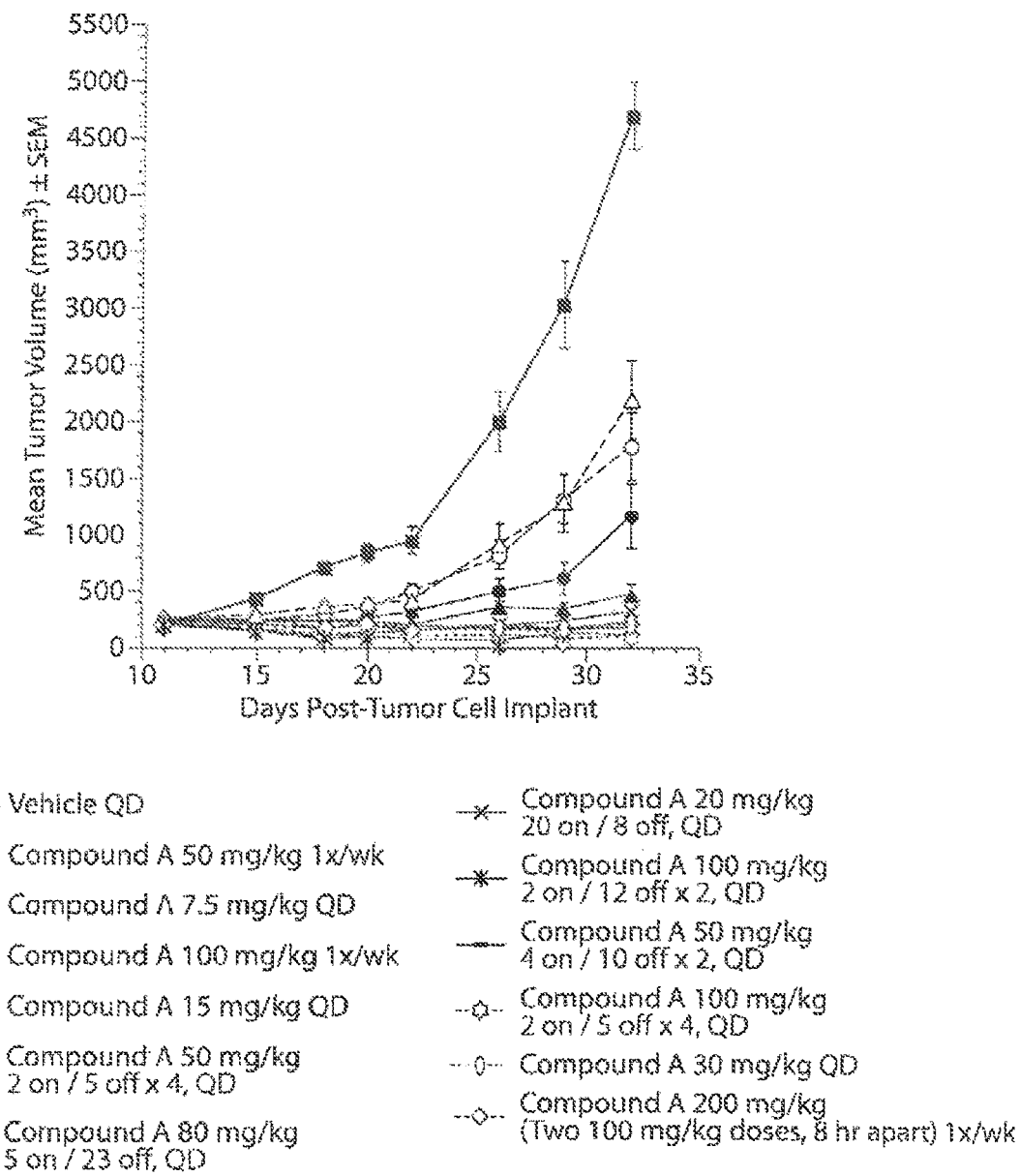
FIG. 1 illustrates the antitumor activity, as demonstrated by the change in mean tumor volume over time, of Compound A monotherapy for a number of different dosing schedules, including a continuous 5 day dosing schedule.

"Tumor control" means that the perpendicular diameters of measurable lesions have not increased by 25% or more from the last measurement. See, e.g., World Health Organization ("WHO") Handbook for Reporting Results of Cancer Treatment, Geneva (1979). The determination of tumor control or shrinkage (also referred to as "regression") is made by known methods. For example, by evaluation of patient symptoms, physical examination, X-ray, MRI or CAT scan or other commonly accepted evaluation modalities.

The present invention relates to a method of treating a patient suffering with cancer, in particular colon, breast, prostate or kidney cancer as well as osteo or tissue sarcoma, comprising administering to the patient Compound A in an amount of from about 800 to about 3000 mg/day, or from about 1000 to about 2500 mg/day, or from about 1250 to about 1800 mg/day, for an administration period of up to about 7 days, preferably up to about 5 days, on days 1-7, or preferably days 1-5, of a 28 day treatment cycle, followed by a rest period of from about 21 to about 23 days, preferably up to about 23 days. The course of a preferred cycle is about 28 days, though cycles anywhere between about 14 and about 28 days are contemplated. This treatment cycle is repeated for as long as the tumor remains under control and the regimen is clinically tolerated.

Dosages of Compound A can be applied either as a body surface area ("BSA") adapted dose (mg/m²/day) or following flat dosing (mg/day). Compound A may be administered as a single dose daily or divided into multiple daily doses.

A patient's body measurement in square meters ("m²") typically ranges from about 1.4 m² to about 2.2 m². Thus, the total amount of Compound A to be delivered in a treatment cycle (mg) using a BSA adapted dose would be calculated as follows:

[Dose intensity(mg/m²/week)]×[BSA(m²)]×[number of weeks in treatment cycle].

In an embodiment, Compound A is administered daily for about 5 days, on days 1-5 of a treatment cycle, followed by a rest period of 23 days ("5+/23−"). The 5+/23− treatment schedule is expected to be superior to interim schedules or to longer schedules as currently on-going Phase I studies indicate that in solid tumors, maximal apoptosis occurs only after about 48 hours of continuous exposure and longer schedules seem to present occurrence of delayed thrombocytopenia ("TCP"). Thus, a 3-5 daily treatment schedule is expected to provide the best benefit ratio taking into consideration efficacy and toxicity Compound A is administered daily, either once or twice (bid) daily, preferably once daily. The compound is administered to the patient in an oral unit dosage form, most preferably in tablet form.

Preferably, the 5 day treatment schedule is repeated every twenty-eight days, or as soon as permitted by recovery from toxicity, for so long as the tumor is under control or regressing and the patient tolerates the regimen. Preferably, these treatment cycles are repeated for a total of up to about 12 cycles.

In an embodiment, Compound A is administered daily in an amount from about 800 to about 3000 mg/day for up to about 5 days on days 1-5 of a 28 day cycle.

In another embodiment, Compound A is administered daily in an amount from about 1000 to about 2500 mg/day for up to about 5 days on days 1-5 of a 28 day cycle.

In another embodiment, Compound A is administered daily in an amount from about 1250 to about 1800 mg/day for up to about 5 days on days 1-5 of a 28 day cycle.

The present invention may be exemplified by controlled preclinical animal studies as shown in the Examples below, which illustrates the invention without limitation.

EXAMPLES

The superiority of the 5 day regimen of the present invention on solid tumors is demonstrated by the following experiments.

Abbreviations used herein are as follows:

| | |
|---|---|
| x | times |
| po | orally |
| bid | twice daily |
| wk | week |
| qd | once daily |
| qd×5 | once daily for five days |
| qweekly or 1×/wk | once a week |
| BWL | body weight loss |
| SD | standard deviation |

Toxicity

In the examples below, weight loss was graphically represented as percent change in mean group body weight, using the formula: $((W-W_0)/W_0) \times 100$, where 'W' represents mean body weight of the treated group at a particular day, and '$W_0$' represents mean body weight of the same treated group at initiation of treatment. Maximum weight loss was also represented using the above formula, and indicated the maximum percent body weight loss that was observed at any time during the entire experiment for a particular group. Toxicity is defined as ≥20% of mice in a given group demonstrating ≥20% body weight loss and/or death.

Tumor Growth Inhibition (TGI) and Assessment of Survival/Increase in Life Span (ILS)

Efficacy data was graphically represented as the mean tumor volume ±standard error of the mean (SEM). In addition, tumor volumes of treated groups were presented as percentages of tumor volumes of the control groups (% T/C), using the formula: $100 \times ((T-T_0)/(C-C_0))$, where T represented mean tumor volume of a treated group on a specific day during the experiment, $T_0$ represented mean tumor volume of the same treated group on the first day of treatment; C represented mean tumor volume of a control group on the specific day during the experiment, and $C_0$ represented mean tumor volume of the same treated group on the first day of treatment.

Tumor volume (in cubic millimeters) was calculated using the ellipsoid formula: $(D \times (d^2))/2$, where "D" represents the large diameter of the tumor and "d" represents the small diameter. In some cases, tumor regression and/or percent change in tumor volume was calculated using the formula: $((T-T_0)/T_0) \times 100$, where 'T' represents mean tumor volume of the treated group at a particular day, and '$T_0$' represents mean tumor volume of the same treated group at initiation of treatment.

Statistical analysis was determined by the rank sum test and One Way Anova and a post-hoc Bonferroni t-test (SigmaStat, version 2.0, Jandel Scientific, San Francisco, Calif., USA). Differences between groups were considered to be significant when the probability value (p) was ≤0.05.

For survival assessment, the percent of increased life space (ILS) was calculated as: 100×[(median survival day of treated group−median survival day of control group)/median survival day of control group]. Median survival was determined utilizing Kaplan Meier survival analysis. Survival in treated groups was statistically compared with the vehicle group and survival comparisons were done between groups using the log-rank test (Graph Pad Prism, La Jolla, Calif., USA). Differences between groups were considered significant when the probability value (p) was ≤0.05.

Example 1

The antitumor activity of Compound A in the human osteosarcoma cancer xenograft model SJASA1 in immuno-compromised mice using a variety of different schedules was assessed.

A. Test Compound A

Compound A was formulated as an amorphous solid dispersion micro-bulk precipitate (MBP) powder containing 30% drag substance and 70% HPMC-AS polymer was reconstituted immediately before administration as a suspension in Klucel/Tween, and remaining suspension was discarded after dosing. All dose levels are reported as the actual dosage of Compound A rather than including drug plus polymer.

B: In Vivo Assays

Animals

Female athymic Crl:NU~Foxn1nu mice (10/group), obtained from Charles River Laboratories (Wilmington, Del.) were utilized when they were approximately 10-12 weeks of age and weighed 23-25 g. The health of the mice was assessed daily by gross observation and analyses of blood samples taken from sentinel animals housed on shared shelf racks. All animals were allowed to acclimate and recover from any shipping-related stress for a minimum of 72 hours prior to experimental use. Autoclaved water and irradiated food (5058-ms Pico Lab mouse chow, Purina Mills, Richmond, Ind.) were provided ad libitum, and the animals were maintained on a 12 hour light and dark cycle. Cages, bedding and water bottles were autoclaved before use and changed weekly. All animal experiments were conducted in accordance with the Guide for the Care and Use of Laboratory Animals, local regulations, and protocols approved by the Roche Animal Care and Use Committee in an AAALAC accredited facility.

Tumors

SJSA cells (ATCC) were maintained in RPMI 1640+10% (v/v) heat-inactivated PBS+1% (v/v) 200 nM L-glutamine. Each mouse received $5 \times 10^6$ cells in a 1:1 mixture of phosphate buffered saline and Matrigel in a total volume of 0.2 ml. Cells were implanted subcutaneously in the right flank using a 1 cc syringe and a 26 gauge needle.

Study Design:

The doses selected for Compound A and schedules utilized in this study are shown in Table 1 below.

TABLE 1

Study Design

| Tumor Model | Treatment Groups |
|---|---|
| SJSA | 1. Vehicle qd po<br>2. Compound A 7.5 mg/kg qd po<br>3. Compound A 15 mg/kg qd po<br>4. Compound A 30 mg/kg qd po<br>5. Compound A 20 mg/kg 20 days qd po, 8 days off<br>6. Compound A 50 mg/kg 1×/week po<br>7. Compound A 100 mg/kg 1×/week po<br>8. Compound A 200 mg/kg (given as two 100 mg/kg doses 8 hours apart (bid)), 1×/week pa<br>9. Compound A 50 mg/kg 4 days qd po, 10 days off × 2 cycles<br>10. Compound A 50 mg/kg 2 days qd po, 5 days off × 4 cycles<br>11. Compound A 100 mg/kg 2 days qd po, 5 days off × 4 cycles<br>12. Compound A 80 mg/kg 5 days qd po, 23 days off<br>13. Compound A 100 mg/kg 2 days qd po, 12 days off × 2 cycles |

Treatment

Compound A was administered orally (po) using a 1 cc syringe and 18-gauge gavage needle (0.2 ml/animal). Treatment duration was 2-4 weeks. Dates of tumor implant, treatment initiation (study start date), and termination of treatment (study end date) can be found in Table 6 below. The starting tumor volume for this study was about 220 mm$^3$. Tumor volumes and animal body weights were measured three times per week and animals were monitored for clinical signs daily.

Figure 2:
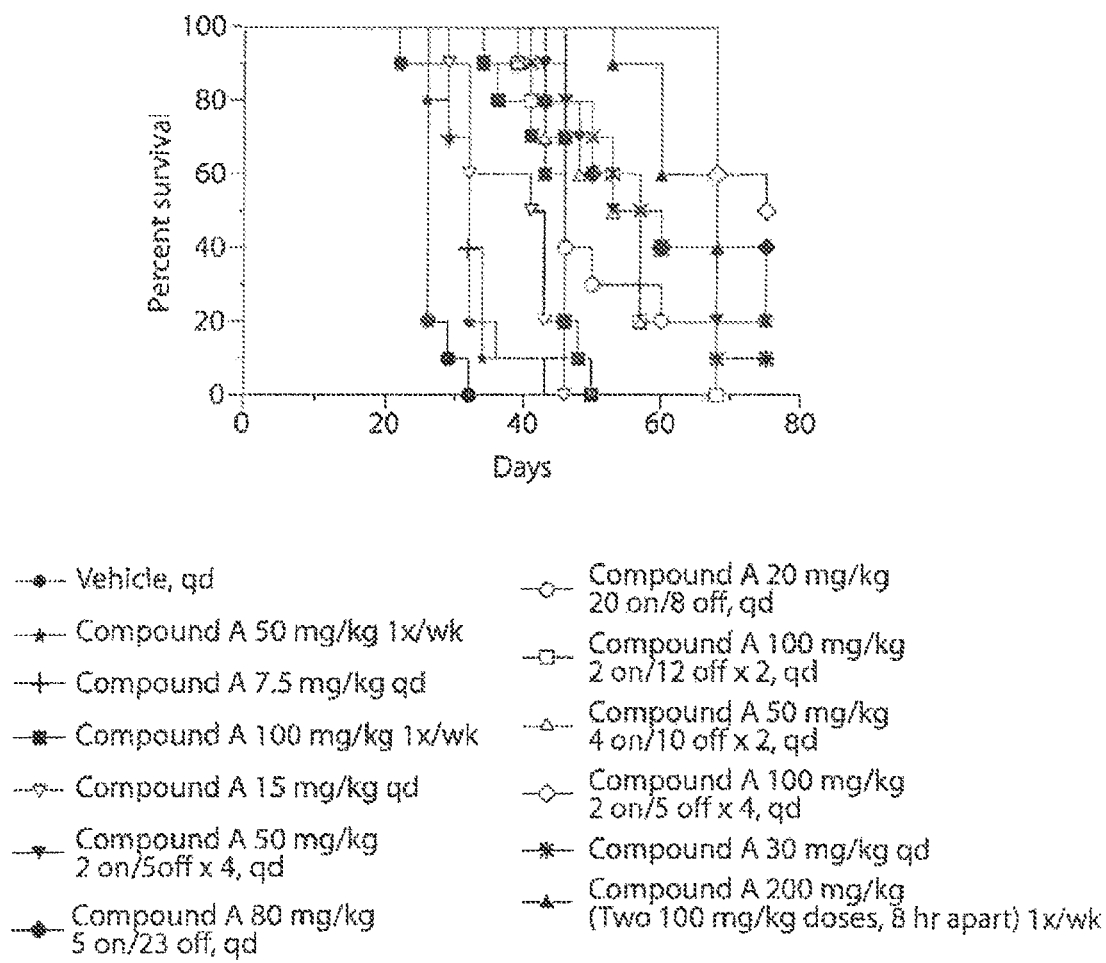
FIG. 2 shows the increased lifespan of mice treated with Compound A for the different dosing schedules also reflected in FIG. 1.

The results of this experiment are summarized Tables 1-3 below and FIGS. 1 and 2. As can be seen, the 5 day treatment schedule yielded the greatest percent increase in life span (% ILS) as well as high percent tumor growth inhibition (% TGI) with reasonable toxicity. FIG. 1 also shows good growth inhibitory activity of the 5 day on/23 day off treatment schedule.

TABLE 2

| Group | Frequency | % Change in Body Weight at end of Study Day 29 | Maximum % Weight loss | Maximum % Weight gain | # of animals ≥20% BWL | Mortality |
|---|---|---|---|---|---|---|
| Vehicle | QD | 13.0 | −1.2 | 13.0 | 0 | 0 |
| Compound A 100 mg/kg | 1×/wk | 9.1 | 4.2 | 9.1 | 0 | 0 |
| Compound A 200 mg/kg (Two 100 mg/kg doses 8 hr apart | 1×/wk | 6.3 | 1.9 | 6.3 | 0 | 0 |
| Compound A 50 mg/kg | 2 on/5 off × 4, QD | 7.1 | −0.8 | 7.1 | 0 | 0 |
| Compound A 80 mg/kg | 5 on/23 off, QD | 8.0 | 0.3 | 8.0 | 0 | 0 |
| Compound A 20 mg/kg | 20 on/8 off, QD | 1.2 | −3.9 | 1.2 | 0 | 0 |
| Compound A 100 mg/kg | 2 on/12 off × 2, QD | 0.9 | −0.6 | 1.8 | 0 | 0 |
| Compound A 50 mg/kg | 4 on/10 off × 2, QD | 1.2 | −1.1 | 1.2 | 0 | 0 |
| Compound A 15 mg/kg | QD | 5.9 | −2.2 | 5.9 | 0 | 0 |
| Compound A 100 mg/kg | 2 on /5 off × 4, QD | 1.3 | −2.8 | 1.3 | 0 | 0 |
| Compound A 30 mg/kg | QD | 1.3 | −0.2 | 1.3 | 0 | 0 |
| Compound A 50 mg/kg | 1×/wk | 6.6 | −0.3 | 6.6 | 0 | 0 |
| Compound A 7.5 mg kg | QD | 9.0 | −0.3 | 9.0 | 0 | 0 |

TABLE 3

Efficacy Summary (left side)

| Group Vehicle or Compound A | Frequency | Mean Tumor (mm3) Start Study Day: 11 | SEM | SD | Mean Tumor Volume (mm3) End Study Day: 32 | SD | SEM |
|---|---|---|---|---|---|---|---|
| Vehicle | QD | 215.03 | ±19.00 | ±60.08 | 4696.49 | ±785.28 | ±296.91 |
| 50 mg/kg | 1×/week | 275.41 | ±22.66 | ±71.65 | 22.66 | ±1103.00 | ±348.80 |
| −7.5 mg/kg | QD | 240.88 | ±18.01 | ±56.95 | 18.01 | ±956.45 | ±302.46 |
| 100 mg/kg | 1×/week | 193.61 | ±9.67 | ±30.57 | 474.73 | ±273.78 | ±86.58 |
| 15 mg/kg | QD | 232.37 | ±16.42 | ±51.93 | 16.42 | ±872.83 | ±276.01 |

TABLE 3-continued

| | | | | | | | |
|---|---|---|---|---|---|---|---|
| 50 mg/kg | 2 on/5 off × 4, QD | 203.43 | ±18.78 | ±59.39 | 257.29 | ±102.12 | ±32.29 |
| 80 mg/kg | 5 on/23 off, QD | 197.38 | ±12.80 | ±40.48 | 128.05 | ±84.89 | ±26.84 |
| 20 mg/kg | 20 on/8 off, QD | 207.20 | ±16.97 | ±53.67 | 315.19 | ±277.51 | ±87.76 |
| 100 mg/kg | 2 on/12 off × 2, QD | 201.40 | ±9.86 | ±31.18 | 179.88 | ±154.02 | ±48.71 |
| 50 mg/kg | 4 on/10 off × 2, QD | 213.61 | ±12.09 | ±38.23 | 244.70 | ±240.07 | ±75.92 |
| 100 mg/kg | 2 on/5 off × 4, QD | 190.78 | ±25.68 | ±81.22 | 25.68 | ±15.82 | ±5.00 |
| 30 mg/kg | QD | 250.86 | ±19.35 | ±61.19 | 19.35 | ±159.01 | ±50.28 |
| 100 mg/kg | 200 mg/kg (Two 100 mg/kg doses, 8 hr apart) × 1× | 224.88 | ±12.02 | ±38.02 | 158.95 | ±68.86 | ±21.78 |

Efficacy Summary Continued (right side)

| % T/C End of Study Day: 32 | % Inhibition end of study Day: 32 | p value end of study Day: 32 | Average % Regression per Group | Partial Regression | Full Regression | Animal per Group | % Increased Life Span | p Value versus Vehicle |
|---|---|---|---|---|---|---|---|---|
| — | — | — | — | 0 | 0 | 7 | — | — |
| 43 | 57 | <0.001 | — | 0 | 0 | 10 | 23 | 0.0036 |
| 34 | 66 | <0.001 | — | 0 | 0 | 10 | 23 | 0.0012 |
| 6 | 94 | <0.001 | — | 1 | 0 | 10 | 77 | <0.0001 |
| 21 | 79 | <0.001 | — | 0 | 0 | 10 | 62 | <0.0001 |
| 1 | 99 | <0.001 | — | 3 | 0 | 10 | 119 | <0.0001 |
| -2 | regression | <0.001 | 35 | 6 | 2 | 10 | 127 | <0.0001 |
| 2 | 98 | <0.001 | — | 5 | 0 | 10 | 77 | <0.0001 |
| 0 | regression | <0.001 | 11 | 7 | 0 | 10 | 119 | <0.0001 |
| 1 | 99 | <0.001 | — | 6 | 0 | 10 | 112 | <0.0001 |
| -2 | regression | <0.001 | 47 | 9 | 0 | 10 | 188 | <0.0001 |
| -1 | regression | <0.001 | 13 | 7 | 0 | 10 | 127 | <0.0001 |
| -1 | regression | <0.001 | 29 | 7 | 0 | 10 | 162 | <0.0001 |

TABLE 4

Survival Summary

| Group | | 50% Treatment Days | 50% Vehicle days | % ILS | p value |
|---|---|---|---|---|---|
| Vehicle | QD | — | — | — | — |
| Compound A 100 mg/kg | 1×/wk | 46 | 26 | 77 | <0.0001 |
| Compound A 200 mg/kg | Two 100 mg/kg doses, 8 hr apart 1×/wk | 68 | 26 | 162 | <0.0001 |
| Compound A 50 mg/kg | 2 on/5 off × 4, QD | 57 | 26 | 119 | <0.0001 |
| Compound A 80 mg/kg | 5 on/23 off, QD | 59 | 26 | 127 | <0.0001 |
| Compound A 20 mg/kg | 20 on /8 off, QD | 46 | 26 | 77 | <0.0001 |
| Compound A 100 mg/kg | 2 on/12 off × 2, QD | 57 | 26 | 119 | <0.0001 |
| Compound A 50 mg/kg | 4 on/10 off × 2, QD | 55 | 26 | 112 | <0.0001 |
| Compound A 15 mg/kg | QD | 42 | 26 | 62 | <0.0001 |
| Compound A 100 mg/kg | 2 on/5 off × 4, QD | 75 | 26 | 188 | <0.0001 |
| Compound A 30 mg/kg | QD | 59 | 26 | 127 | <0.0001 |
| Compound A 50 mg/kg | 1×/wk | 32 | 26 | 23 | 0.0036 |
| Compound A 7.5 mg/kg | QD | 32 | 26 | 23 | 0.0012 |

Overall, the 5 days on and 23 days off (5+/23−) schedule is predicted to reduce MDM2 inhibitor-induced thrombocytopenia in humans undergoing treatment for solid tumors, while still maintaining antitumor efficacy, as compared to other regimens considered.

What is claimed:

1. A method of treating a patient suffering form cancer, comprising administering to said patient a pharmaceutical composition containing as an active ingredient 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid (Compound A) in an amount from about 800 mg/day to about 3000 mg/day, daily, for up to about 7 days, followed by a rest period of up to about 21 days, said administration starting on the first day of a 28 day treatment cycle.

2. A method of treating a patient suffering form cancer, comprising administering to said patient a pharmaceutical composition containing as an active ingredient 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid (Compound A) in an amount from about 800 mg/day to about 3000 mg/day, daily, for up to about 5 days, followed by a rest period of up to about 23 days, said administration starting on the first day of a 28 day treatment cycle.

3. The method of claim 2 wherein Compound A is administered in an amount from about 1000 mg/day to about 2500 mg/day.

4. The method of claim 3 wherein Compound A is administered in an amount of from about 1250 mg/day to about 1800 mg/day.

5. The method of claim 1 wherein the treatment cycle being repeated every 28 days for up to about 12 cycles.

6. The method of claim 1 wherein Compound A is administered twice daily in equal doses.

7. The method of claim 1 wherein the cancer is colorectal cancer.

8. The method of claim 1 wherein the cancer is prostate cancer.

9. The method of claim 1 wherein the cancer is lung cancer.

10. The method of claim 1 wherein the cancer is kidney cancer.

11. The method of claim 1 wherein the cancer is breast cancer.

* * * * *